US00PP32262P2

(12) United States Plant Patent
Hansen

(10) Patent No.: US PP32,262 P2
(45) Date of Patent: Sep. 29, 2020

(54) ***KNIPHOFIA* PLANT NAMED 'GOLD RUSH'**

(50) Latin Name: ***Kniphofia* hybrid**
Varietal Denomination: Gold Rush

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,020

(22) Filed: Jan. 15, 2020

(51) Int. Cl.
*A01H 5/02* (2018.01)

(52) U.S. Cl.
USPC ..... Plt./443

(58) Field of Classification Search
USPC ..... Plt./443
See application file for complete search history.

*Primary Examiner* — Annette H Para

(57) ABSTRACT

A new and distinct cultivar of ornamental Red Hot Poker, *Kniphofia* plant named 'Gold Rush', with long, gracefully-arching, strap-like, keeled, glaucous, gray-green foliage and numerous scapes beginning in late summer with rebloom under optimal growing conditions. Habit is densely-growing, winter-hardy and tolerant of heat. Numerous scapes with dense flowers of intense bright yellow buds that retain their color when flowers open. The new plant is useful for landscaping as a specimen, en masse, or as a long-lasting cut flower.

1 Drawing Sheet

Botanical classification: *Kniphofia* hybrid.
Variety denomination: 'Gold Rush'.

STATEMENT REGARDING PRIOR DISCLOSURES UNDER 37 CFR 1.77(B)(6)

The first non-enabling disclosure of the claimed plant, in the form of a photograph and brief description, was made by Walters Gardens, Inc. on Feb. 1, 2019 on their website. Subsequently, on May 29, 2019, the claimed plant was displayed with a photograph and brief sales promotion on the "Walters Gardens 19-20 Catalog." Walters Gardens, Inc. sold the first plants on Sep. 23, 2019. Walters Gardens, Inc. obtained the new plant and all information relating thereto, from the inventor. No plants of *Kniphofia* 'Gold Rush' have been sold, in this country or anywhere in the world nor has any disclosure of the new plant been made more than one year prior the filing date of this application, and any such sale or disclosure of the new plant within one year was either derived directly or indirectly from the inventor.

BACKGROUND AND ORIGIN OF THE PLANT

The present invention relates to the new and distinct Red Hot Poker, *Kniphofia* 'Gold Rush' developed under the direction of the inventor at a wholesale perennial nursery in Zeeland, Mich., USA in the summer of 2013. The new plant was the result of a single seedling selection from a cross of 'Sally's Comet' (not patented) as the female or seed parent and 'Echo Mango' U.S. Plant Pat. No. 21,706 as the male or pollen parent performed on Jul. 9, 2013. The plant passed initial evaluation in the summer of 2015 and was subsequently given the breeder code 13-4-2 prior to naming. *Kniphofia* 'Gold Rush' has been successfully asexually propagated by division method since 2015 at the same wholesale perennial nursery in Zeeland, Mich. and subsequently by shoot tip tissue culture, and both methods have been found to be stable and produce identical plants that maintain the unique characteristics of the original plant through successive generations.

SUMMARY OF THE PLANT

*Kniphofia* 'Gold Rush' differs from its parents as well as all other *Kniphofia* known to the applicant. The most similar known *Kniphofia* cultivars are: 'Solar Flare' U.S. Plant patent application Ser. No. 16/350,525, 'Percy's Pride' (not patented), 'Flashpoint' U.S. Plant Pat. No. 31,282 and 'Pineapple Popsicle' U.S. Plant Pat. No. 22,969. 'Solar Flare' is shorter in scape and foliage and the flower is deeper yellowish, and the flowers begin earlier in the summer. 'Percy's Pride' is taller with more light-yellow to lime-colored flowers and the flower heads are larger. 'Flashpoint' has chartreuse-yellow flower buds that produce flowers of creamy white. 'Pineapple Popsicle' is shorter in scape height, foliage height and overall habit and has a lighter yellow flower buds and fewer flowers per inflorescence. 'Sally's Comet' has a shorter habit and more greenish flower buds with smaller flower heads. 'Echo Mango' has a slightly taller habit and the flowers are more orangish-gold.

*Kniphofia* 'Gold Rush' differs from these above cultivars and all cultivars known to the inventor in that it has:

1. Gracefully arching, strap-like, keeled, gray-green foliage.
2. Rapidly growing, dense habit, winter-hardy, heat tolerant, rabbit and deer tolerant, moderate-sized clumps.
3. Numerous spikes of bright yellow buds on medium height stems that retain their color when open on medium height stems;
4. Flowering beginning late summer for three weeks in Michigan with rebloom in under optimal growing conditions.

BRIEF DESCRIPTION OF THE DRAWINGS

The photographs of *Kniphofia* 'Gold Rush' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
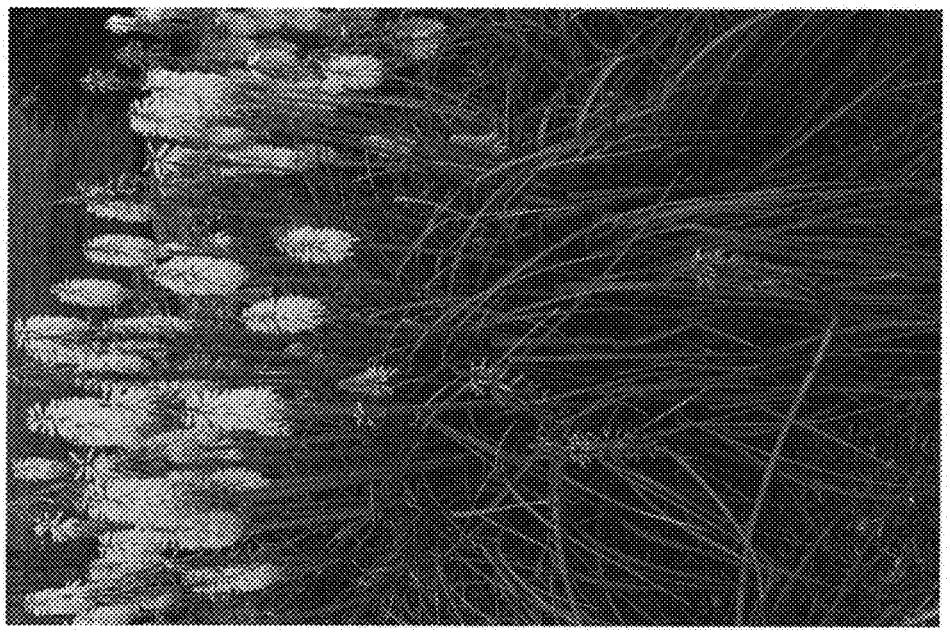
FIG. 1 shows the side-view habit of a five-year-old plant in midseason flowering.
Figure 2:
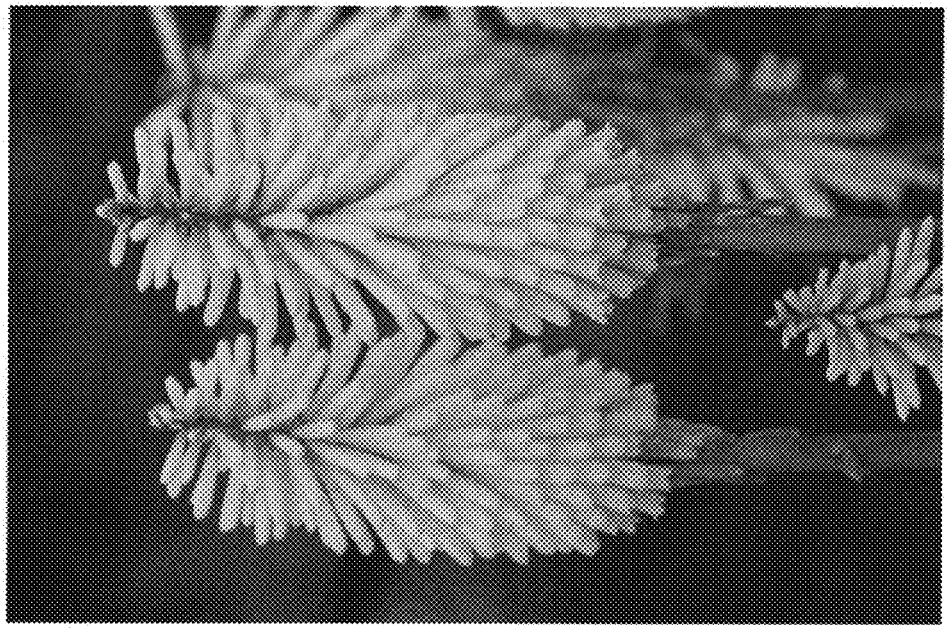
FIG. 2 shows a close-up of the flowers and buds.

The following descriptions and color references are based on the 2015 edition of The Royal Horticultural Society Colour Chart except where common dictionary terms are used. The new plant, *Kniphofia* 'Gold Rush', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Sally's Comet' as the female or seed parent and 'Echo Mango' as the male or pollen parent;

Propagation method: By garden division of the rhizome and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 110.0 cm across and about 54.0 cm tall; flowering to about 112.0 cm tall; about 60 peduncles per plant;

Leaves: Linear; keeled at base, triangular in distal half; arranged up to 12 leaves per basal division; apex narrowly acute; base truncate, clasping; margin entire; no fragrance observed;

Leaf size: To about 112.0 cm long and 32.0 mm across at base, average about 98.0 cm long and 24.0 mm across at base;

Leaf color: Young base nearest RHS NN155C both abaxial and adaxial, distally between RHS 144A and RHS 138A both abaxial and adaxial; mature adaxial between RHS 137A and RHS 137B, abaxial nearest RHS 137B;

Leaf venation: Parallel; color same as leaf abaxial and adaxial;

Stem: Acaulescent; rhizome about 20.0 mm across at base;

Inflorescence: In spike-like raceme; cylindrical; about 250 flowers per stem; flowering portion to about 37.0 cm tall and about 7.0 cm across; lasting about three weeks; flower spacing less than 1.0 mm apart on raceme in distal region and about 2.5 cm in lowest flowers;

Peduncle: Cylindrical; glabrous; glaucous; stiff; upright; solid not fistulose; to about 112.0 cm long and 10.0 mm diameter; average 98.0 cm tall and 9.0 mm diameter; rarely with single branch of up to 15 cm long;

Peduncle color: Basal 2 cm nearest RHS NN155A; distally including branch between RHS 146C and RHS 146B;

Buds one day prior to opening: Tubular with slightly swollen rounded apex and rounded base; glabrous; lustrous; about 27.0 mm long and about 3.0 mm diameter at base and 7.0 mm diameter at widest point near apex;

Bud attitude: Beginning outwardly and drooping as maturing toward anthesis;

Bud color: Abaxial one day prior to opening nearest RHS 5C with midrib nearest RHS 5A;

Flowers: Cylindrical forming tubular corolla; perfect; incomplete; actinomorphic; individually open and effective about three to four days;

Flower size: To about 32.0 mm long to tip of exserted stigma, fused in basal about 24.0 mm; face to about 8.0 mm tall and about 10.0 mm wide; corolla tube about 5.0 mm diameter near base and about 7.5 mm near throat; corolla tube to 28.0 mm long;

Flower attitude: Drooping;

Flower fragrance: None detected;

Flowering period: Individual racemes effective for about 3 weeks; beginning late summer for about three weeks in Michigan;

Tepals: Six, in two identical sets of three; both sets with acute apices and fused in basal 25.0 mm forming tube; margin entire; glabrous and lustrous abaxial and adaxial; about 28.0 mm long and about 3.0 mm across just above fusion point, about 4.0 mm long above fusion;

Tepal color (young and mature adaxial): Both inner and outer sets identical nearest RHS 8D with midribs nearest RHS 13C; (young and mature adaxial): inner and outer sets identical between RHS 5C and RHS 5D with midribs nearest RHS 5A; inner set adaxial and abaxial margins nearest RHS NN155A;

Androecium: Six;

*Filaments*.—Six; exserted; straight; glabrous; lustrous; about 29.0 mm long and about 0.7 mm diameter; color nearest RHS 155C proximally, transitioning in distal 5 mm to between RHS 2B and RHS 2C.

*Anther*.—Six; oblong-ellipsoidal; dorsifixed; longitudinal; about 2.5 mm long and 1.5 mm across and 1.0 mm thick; color nearest RHS N163D.

*Pollen*.—Abundant: color nearest RHS 8B.

Gynoecium: Single; about 32.0 mm long;

*Style*.—Cylindrical; straight; glabrous; lustrous; about 28.0 mm long and 1.0 mm diameter: color nearest RHS 2D.

*Stigma*.—Flattened; about 1.0 mm across; color nearest RHS 2D.

*Ovary*.—Superior; ellipsoidal; rounded apex, truncate base; about 4.0 mm long and 3.0 mm diameter; color nearest RHS N144A.

Pedicel: Cylindrical; glabrous; slightly glaucous; stiff; drooping with maturity; about 2.0 mm long and about 1.0 mm diameter;

Pedicel color: Nearest RHS N170B dorsally and nearest RHS 152D ventrally in proximal flowers and RHS 166B in distal flowers;

Bracts: Deltoid; at cauline nodes and subtending individual flowers; with acute apices and truncate base; to about 7.0 mm long and 4.5 mm across at base; decreasing distally; color nearest RHS 164D;

Fruit: Tri-valved loculicidal capsule; globose to ellipsoidal; about 7.0 mm long and 5.0 mm across; glabrous; with rounded apex and rounded base; typically four to nine seeded; color upon maturity nearest RHS 199A;

Seed: Irregular with angular sides, acute apex and base; about 5.0 mm and 3.0 mm across; color nearest RHS 200A;

Disease and pest resistance: 'Gold Rush' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of *Kniphofia* plant named 'Gold Rush' as herein described and illustrated.

* * * * *